United States Patent
Orlowski et al.

(10) Patent No.: US 6,981,875 B2
(45) Date of Patent: Jan. 3, 2006

(54) CONTACT CURE DENTAL POST CEMENT AND METHOD OF PLACING A DENTAL POST

(75) Inventors: Jan A. Orlowski, Pomona, CA (US); John J. Discko, Jr., Trumbull, CT (US)

(73) Assignees: Centrix, Inc., Shelton, CT (US); Scientific Pharmaceuticals, Inc., Pomona, CA (US)

( * ) Notice: Subject to any disclaimer, the term of this patent is extended or adjusted under 35 U.S.C. 154(b) by 396 days.

(21) Appl. No.: 10/185,072

(22) Filed: Jun. 28, 2002

(65) Prior Publication Data

US 2004/0002037 A1 Jan. 1, 2004

(51) Int. Cl.
A61C 5/08 (2006.01)
A61C 5/00 (2006.01)

(52) U.S. Cl. .................... 433/220; 433/228.1

(58) Field of Classification Search ............. 433/217.1, 433/219, 220, 221, 226, 228.1
See application file for complete search history.

(56) References Cited

U.S. PATENT DOCUMENTS

| | | | | |
|---|---|---|---|---|
| 3,581,399 A | * | 6/1971 | Dragan | 433/90 |
| 4,340,529 A | * | 7/1982 | Lee et al. | 524/105 |
| 4,363,624 A | * | 12/1982 | Johnston | 433/9 |
| 4,771,112 A | | 9/1988 | Engelbrecht | 525/327.3 |
| 4,792,577 A | * | 12/1988 | Chen et al. | 523/118 |
| 4,813,874 A | * | 3/1989 | Jensen | 433/219 |
| 5,883,153 A | * | 3/1999 | Roberts et al. | 523/116 |
| 5,965,632 A | | 10/1999 | Orlowski et al. | 523/116 |
| 5,989,032 A | * | 11/1999 | Reynaud et al. | 433/224 |
| 6,049,934 A | * | 4/2000 | Discko | 15/106 |
| 6,103,800 A | | 8/2000 | Peterson et al. | 524/296 |

FOREIGN PATENT DOCUMENTS

| | | |
|---|---|---|
| JP | 63 175085 | 7/1988 |
| JP | 01 090277 | 4/1989 |
| WO | WO 02/47572 A1 | 6/2002 |

OTHER PUBLICATIONS

Scientific Pharmaceuticals, Inc., Contact Cure Orthodontic Adhesive—Technical Bulletin, 2 pages, 1986.

* cited by examiner

Primary Examiner—Cary E. O'Connor
(74) Attorney, Agent, or Firm—Fattibene & Fattibene; Paul A. Fattibene; Arthur T. Fattibene

(57) ABSTRACT

Securing a dental post or a crown or bridge onto the dentin portion of a prepared tooth by utilizing a no-mix, two component, self-curing cement wherein the first component of the cement is applied to the interior dentin surfaces of a post hole, or onto the dentin surface of the tooth receiving the crown or bridge, and applying the second component of the cement onto the surface of a post, or crown or bridge so that when the post or crown or bridge is fitted onto the exposed dentin of a prepared tooth, the complementary components of the cement immediately chemically set to firmly secure the post, crown or bridge onto the prepared tooth. The respective components of the no-mix, two component, self-curing cement formulation for practicing the method require that each include a methacrylate resin. One of the components also includes an aromatic tertiary amine and the other component includes an organic peroxide. At least one or both of the components also includes hydroxyethyl methacrylate or hydroxypropyl methacrylate or other hydrophilic monomers. Additives such as thickeners, fillers, fluoride salts, and polymerization inhibitors may also be included in one or the other component.

31 Claims, 3 Drawing Sheets

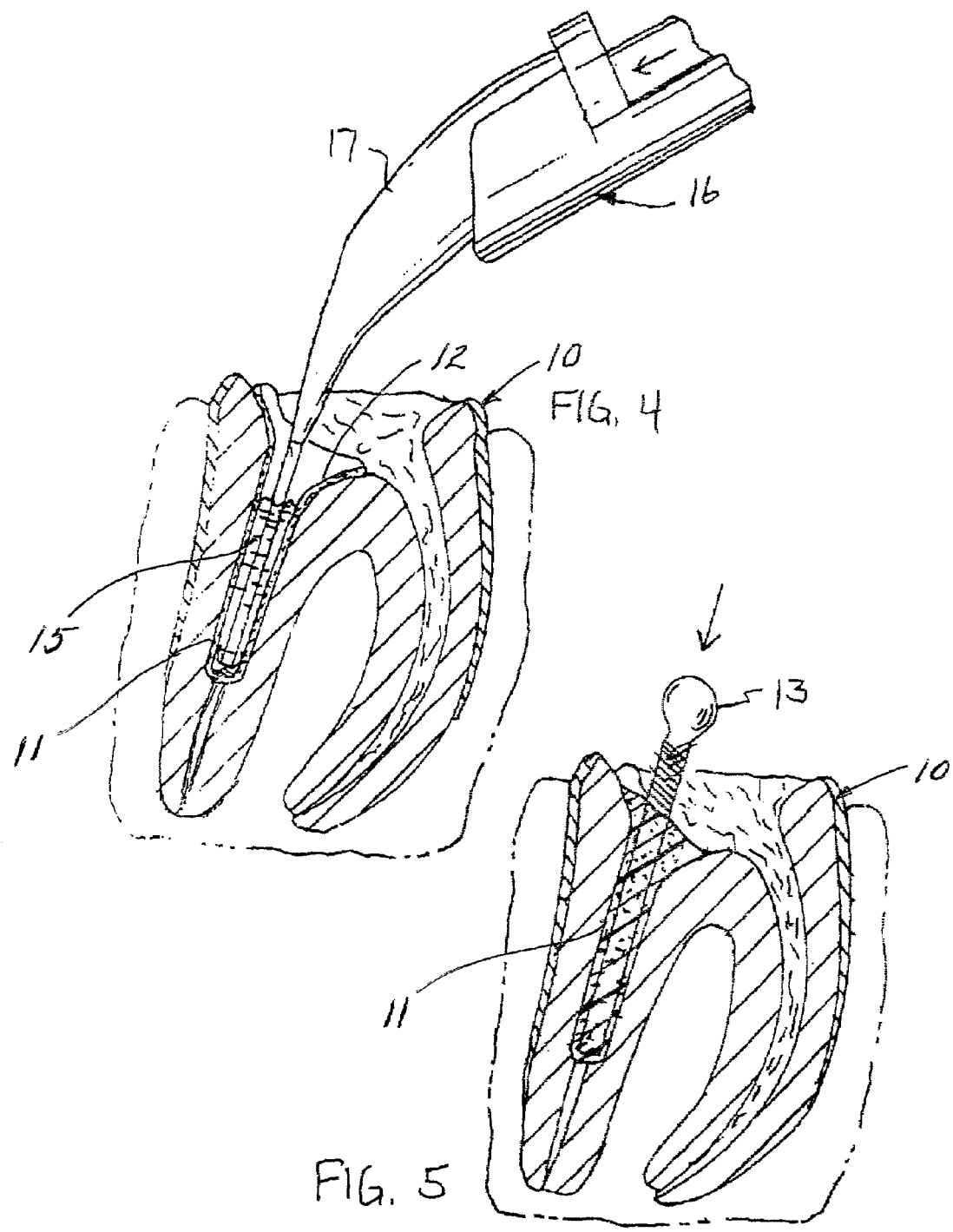

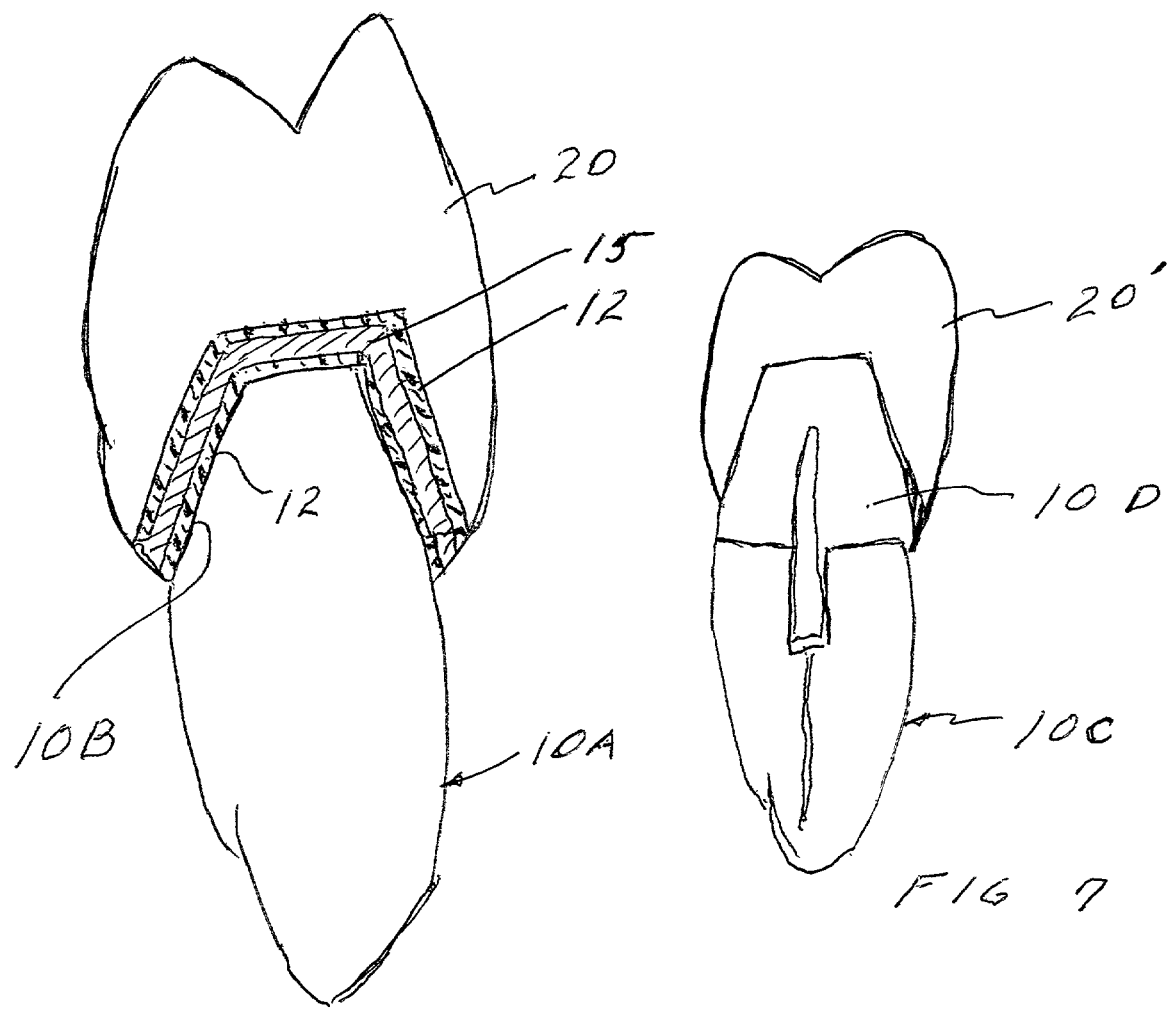

CONTACT CURE DENTAL POST CEMENT AND METHOD OF PLACING A DENTAL POST

FIELD OF THE INVENTION

A contact cure cement for anchoring a dental post or crown in a prepared tooth and a method of securing a dental post or crown in a prepared tooth. More specifically, a "no mix" two-part self curing dental cement and a method for placing a dental post or crown in a prepared tooth quickly and simply.

BACKGROUND OF THE INVENTION

Cements have long been used in dentistry for a variety of purposes including the attachments of dental prosthesis such as crowns and bridges, posts and various other appliances to teeth. Unlike orthodontic appliances, such as orthodontic bands, braces or brackets, which are cemented or bonded primarily to the enamel portion of a tooth; crowns, bridges and dental posts are required to be cemented primarily to the dentin portion of a tooth. Bonding or cementing to dentin presents problems not common to bonding or cementing to tooth enamel. The problem is further aggravated with respect to cementing a dental post in a post hole formed in a tooth to be restored, as such post holes are generally enlarged root canals.

Cemented posts are required to withstand relatively large forces. The known procedures for preparing a post hole limits the options available for increasing post retention by mechanical interlocking. Therefore, post retention must be primarily achieved by friction and/or adhesive forces.

Heretofore, the selection of suitable prior art cements was strictly limited to self curing, two part cements which are required to be mixed shortly before application. The problem encountered with the use of the two part self curing cement required intimate mixing of the two components which limited the amount of working time for effecting the placement of the material before it sets. Further, a dentist had to precisely determine the ratio between the two components to be mixed, to assure proper reproducibility in the setting characteristics and properties of the cured cement, which is frequently difficult to achieve. Too little or too much of one or both of the components forming the mix could adversely effect the curing time, chemical properties and/or strength of the cured cement. The known light cured cements or materials, which provide the convenience of virtually unlimited working time, are not suitable for cementing a dental post in a post hole or placing a crown onto a tooth because of insufficient light penetration and related depth of cure requirements, necessary to achieve strong enough post or crown retention to resist the relatively large forces imparted upon the restored tooth.

The prior known methods of placing a dental post for effecting the replacement or rebuilding a tooth coronal structure generally required the mixing of two components of a self curing cement after the preparing of the post hole in a tooth. After the two components have been mixed, the mixture had to be delivered to the tooth by some means. Depending upon the nature of the mixed cement, it could be manually placed or syringed in the post hole and/or onto the post prior to insertion of the post into the post hole. As the cement was self curing after being mixed, time was of the essence to effect the placement of the post in the post hole and removal of the excess before the cement set. In the case of self curing resin cements, most required the added step of etching and/or applying a bonding agent into the post hole before the self curing cement components were mixed and placed. Thus, the additional step of etching and/or covering the walls of the preparation with a suitable bonding agent was required. The conventional resin cements used for cementing or bonding dental prosthesis such as bands, brackets and braces to the enamel portion of the tooth are not best suitable for cementing dental posts to the dentin portion of a tooth.

SUMMARY OF THE INVENTION

An object of this invention is to provide a two part self curing dental cement which sets on contact and requires no premixing of the two component parts prior to the use thereof.

Another object is to provide a method of placing a dental post in a post hole of a tooth in a simple, expedient and efficient manner.

Another object is to provide a two part self cured dental cement in which no etching and/or special bonding agent is required.

Another object is to provide a method of placing a dental post in the post hole of a tooth in a minimum of time with the result that post is firmly set to resist the forces imparted to the restored tooth.

Another object is to provide that at least one of the cement components may be supplied in a pre-filled capsule or syringe for effecting the placing of the component by a syringing technique to minimize the formation of voids.

Another object is to provide a dental self cure cement having a formula which ensures total polymerization of the cement on contact.

Another object is to provide a dental self cure cement that virtually eliminates the possibility of operator' error and assures consistency of curing times and retentive strength.

Another object is to provide a dental self cured cement that is moisture tolerant.

Another object is to provide a dental, self curing cement wherein any excess of cement may be more easy to move as the displaced excess hardens at a much slower rate.

Another object is to provide for a no-mix, two component, self-curing cement having superior adhesive or holding characteristics.

Another object is to use a no mix, two component, self-curing cement for the cementing of crowns and bridges.

The foregoing objects, features and other advantages, which will become readily apparent, are attained by an improved method of attaching a dental post, bridge or crown or other dental prosthesis to a tooth structure to be restored. The method includes the steps of preparing a tooth to receive a prosthesis, e.g. a dental post, crown or bridge in the usual manner. If desired, after the post hole is drilled or the tooth prepared in the customary manner, a solution of phosphoric acid may be used to condition the prepared tooth, which is then washed and dried. It is understood that other dentin conditioners may be used such as citric, tartaric, polyacrylic, tannic acid, ETDTA and its salts, sodium hypochloride and the like.

In accordance with this invention, a first component of a two part cement, viz. a hydrophilic primer in the form of a liquid, is coated onto the inside surfaces of the post hole. The primer may also be optionally coated on the surface of the post itself. The second component of the self cured cement, which is in the form of a paste, is injected into the post hole, preferably by a syringing technique. The post is then inserted into the post hole whereby the post is cemented in place as a result of the paste coming in firm contact with the liquid cement component. In a matter of a few minutes, e.g. in 1 to 5 minutes, the post is firmly retained so that one cannot twist or pull the post out of the hole. Any excess cement can be easily removed as it tends to harden at a much slower rate than when the components are placed into firm contact.

The preferred self cure cement for practicing the method is a no mix, two components cement that may differ in physical form and chemical composition. Both components preferably should be of a moderately viscous consistency and in a physical form of a moderately viscous liquid or a lightly filled paste. The formulation of the respective components should include a methacrylate resin in a range of 20% to 98% by weight, preferably in the order of 40% to 95% by weight. One of the components should also include 1% to 12% by weight of an aromatic tertiary amine, preferably in the range of 1.8%–8% by weight while the other component should include 0.3% to 5% by weight of organic peroxide, most preferably benzoyl peroxide.

Optionally, the respective components may also contain organic thickeners that are soluble in the resin matrix, an inorganic or organic filler, and other additives which function to enhance post retention, strengthening or protecting the tooth structure, and/or enhancing the handling characteristics. The formulation of at least one of the components should also include at least 1 to 25% by weight of hydrophilic monomers, such as hydroxyethyl or hydoxypropyl methacrylate, which is desirable for ensuring better residual moisture tolerance, and improved adhesive qualities.

The formulation may also contain in either component other additives that have a beneficial effect on the health of the tooth or the stability of the formulation, e.g. various fluoride compounds for enhancing resistance to tooth decays. Also, other types of additives may be incorporated, such as polymerization inhibitors that will enhance the cement's resistance to adverse storage conditions.

Other features and advantages will become readily apparent in view of the following detailed description.

IN THE DRAWINGS

FIG. 4 illustrates a sectional view similar to that of FIG. 2, illustrating the step of placing the second component of the two part cement in the prepared post hole.

FIG. 5 illustrates a section view similar to FIG. 4 with the dental post firmly secured in the post hole.

FIG. 6 is a partial sectional view of a crown or bridge being secured to a prepared tooth in accordance with this invention.

FIG. 7 is a view similar to FIG. 6, illustrating a crown or bridge secured to a tooth having a core build-up in accordance with this invention.

DETAILED DESCRIPTION

Figure 1:
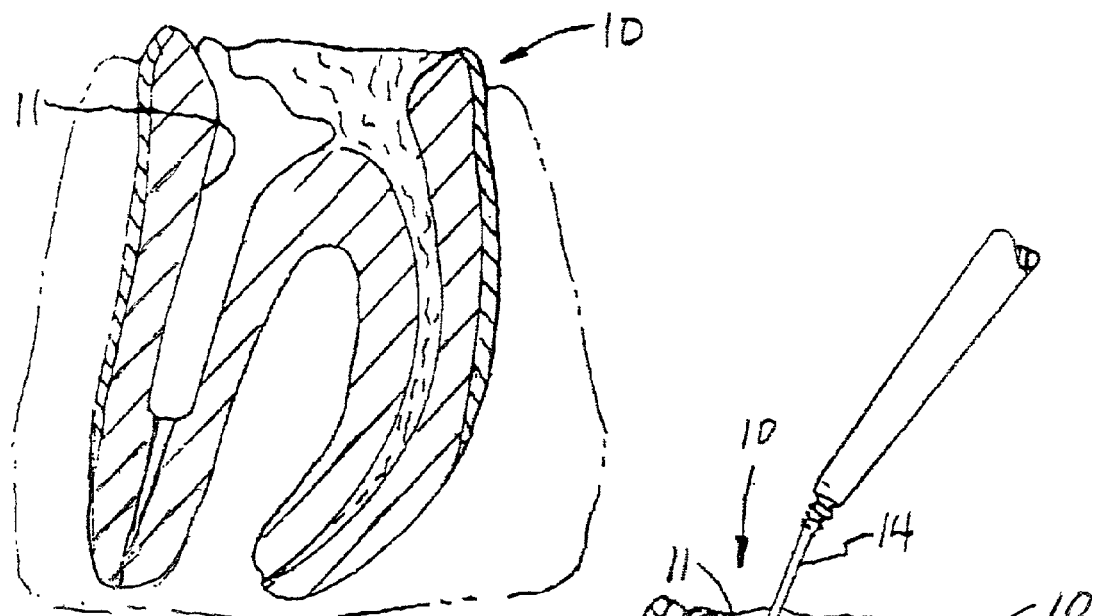
FIG. 1 illustrates a sectional view of a prepared tooth formed with a post hole for receiving a dental post.

Referring to the drawings, there are illustrated the various steps for practicing the method of placing a dental post in a prepared tooth in accordance with this invention. FIG. 1 illustrates a sectional view of a tooth 10 having formed therein a post hole 11. It will be understood that the post hole 11 is prepared or formed in the conventional manner. Generally, it may comprise simply the enlargement of the tooth's root canal which extends through the dentin portion of the tooth. After the post hole 11 has been drilled or formed, it may be cleaned with a suitable conditioner to remove any loose debris, which is then followed by rinsing with water and drying. Such cleaning agents may include a solution of phosphoric acid, EDTA, alcohol or other suitable dentin cleaning agent.

The inner surface of the post hole 11 is then coated with a hydrophilic primer 12, which comprises the first component of the cement, as will be hereinafter described. As the hydrophilic primer 12 is in the form of a moderately viscous liquid, it is preferred that the primer 12 be applied by means of a micro brush 14 of the types disclosed in U.S. Pat. Nos. 6,186,792 B1 and 6,049,934, incorporated herein by reference, or any other micro size applicator capable of placing the hydrophilic primer 12 in a post hole 11. Other methods may be used to coat the inner surface of the post hole as well.

Figure 3:
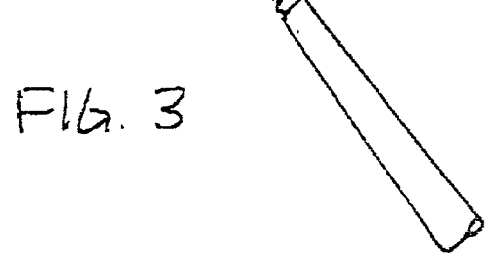
FIG. 3 illustrates the optional step of coating the dental post with the primer or first component of the two part cement of the described invention.

The outer surface of the dental post 13 may also be coated with a layer of the hydrophilic primer component 12, by means of the micro brush 14, as noted in FIG. 3.

Figure 2:
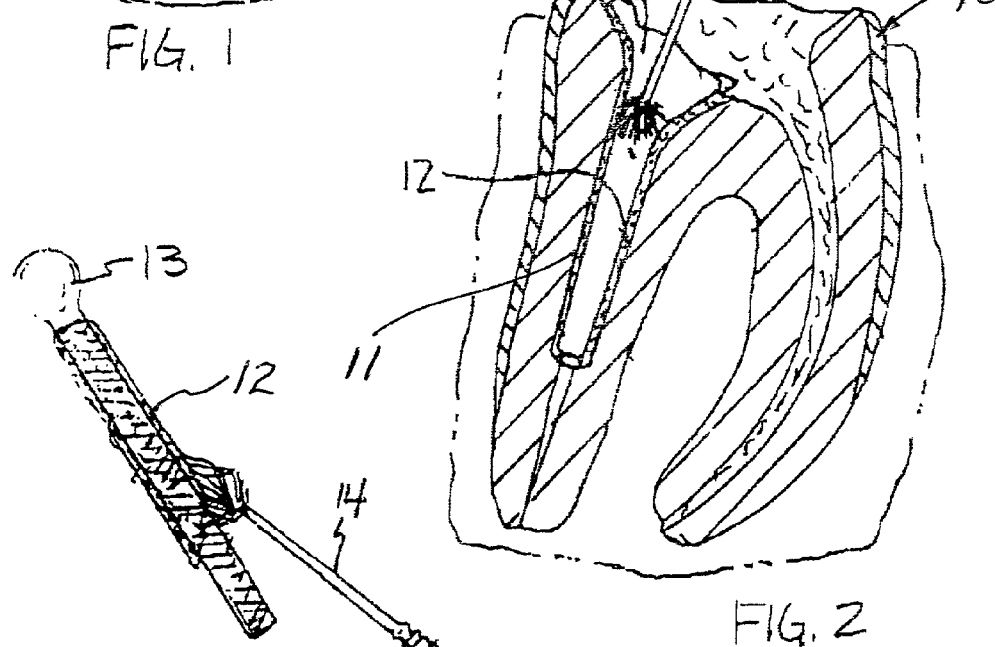
FIG. 2 is a sectional view similar to FIG. 1, illustrating the lining of the post hole with a primer or first component of a two part cement of the described invention.

Upon the placement of the hydrophilic primer 12 onto the inner surfaces of the post hole 11, as shown in FIG. 2, the second component 15 of the cement is positioned in the post hole 11. As best seen in FIG. 4, it is preferred that the second component 15 of the cement be placed in the post hole by means of a Centrix type syringe 16 of the type disclosed in U.S. Pat. Nos. 3,581,399; 4,198,756, and 5,083,921, using a needle tip capsule 17 of the type disclosed in U.S. Pat. No. 5,052,927, all of which are incorporated herein by reference. It will be understood that any other suitable device may also be used for injecting the second component 15 of the cement into the post hole 11. The amount of the second component 15, which is syringed into a post hole, should be sufficient so that when displaced upon the insertion of the post 13, will occupy any remaining space between the post 13 and the inner wall of the post hole 11.

With the first and second components 12 and 15 so positioned within the post hole 11, the post 13 is then immediately set into the post hole, as seen in FIG. 5, before the components of the cement are allowed to set. Upon the placement of the post 13, the components 12 and 15 will immediately set in a matter of minutes. For example, within 1 to 5 minutes, the post 13 is firmly cemented and fixed in place.

Alternately, the method of placing the post 13 in the post hole 11 in a prepared tooth can be effected by coating the surface of the post 13 with one of the components, and coating the post hole 11 with the other component. Upon inserting the coated post 13 into the coated post hole, the respective components set upon contact to firmly retain or secure the post 13 within the post hole 11.

In accordance with this invention, it will be noted that no pre-mixing of the two components 12 and 15 prior to use is required. As a result, the post 13 may be placed and set in a minimum of time and with a minimum of effort. As will hereinafter be set forth, the cement formulation includes a hydrophilic monomer, which renders the cement especially desirable because of its residual moisture tolerance and improved adhesive characteristics to dentin.

The preferred cement for practicing the described method comprises two components which require no pre-mixing prior to use. The two components differ in their physical form and basic chemical composition. Both components should preferably be of a moderately viscous consistency and in a physical form of a moderately viscous liquid or a lightly filled paste.

Generally, the cement formulation includes 20% to 98% by weight of a methacrylate resin, preferably 40% to 95% by weight and 1% to 12% of an tertiary aromatic amino, preferably 2.5% to 8% by weight being incorporated in one of the components while the other component contains 0.3% to 5% by weight of an organic peroxide, preferably benzoyl peroxide. Optionally, the cement formulation may also contain organic thickeners that are soluble in the resin matrix, inorganic or organic fillers and other additives which function to provide enhanced post retention, strengthening or protection of the tooth and/or enhanced handling characteristic.

Examples of suitable resins for use in the formulation of the cement of this invention include: Diglycidyl ether of bis-phenol A dimethacrylate (which is commonly known in the industry as Bis-GMA); alkylene glycol dimethacrylates, such as ethylene, diethylene, triethylene and polyethylene glycol trimethacrylate, trimethylolopropane trimethacrylate; hydroxyethyl methacrylate; hydroxypropyl methacrylate; tetrahydrofurfuyl methacrylate; Bis-phenol A dimethacrylate; 7,7,9-trimethylo-4,13 dioxo-3,4-dioxa-5 diazahexadecane-1,6 diol dimethacrylate (known in the industry as diurethane dimethacrylate) hexanediol dimethacrylate and cyclohexanediol dimethacrylate.

The tertiary aromatic amines, which serve as polymerization activators, include N,N Bis(2-hydroxyethylo)-p-toluidine; N,N Bis(2-hydroxypropylo),-p toluidine; N,N dimethylo-p-toluidine; N,N-diethylo-p-toluidine and similar compounds.

The formulation of the instant cement preferably includes hydrophilic monomers, such as hydroxyethyl or hydroxypropyl methacrylate in the range of 1% to 25% by weight, preferably at least 10% by weight. These monomers are especially desirable for their residual moisture tolerance and adhesive characteristics.

The desired thickening agents for use in the cement formulation of the instant cement include polyacrylic acid having a molecular weight of about 200,000, polyalkylene such as polybutenes and poly-C1–C3 alkyl methacrylates.

The fillers suitable for use in either component of the instant cement formulation may include various types of glasses, quartz, zirconium oxide, silica, aluminum oxide, polyethylene, barium sulfate, calcium sulfate, titanium oxide, calcium phosphate, calcium silicate (Wollastonite) diatomaceous earth and bentonite. The particle size of the fillers should range between 0.05 microns to 70 microns.

The cements of this invention may also contain, in either of its parts, additives which can have a beneficial effect on the health of the tooth or on the stability of the formulation. Such additives may include fluoride salts, such as sodium fluoride, stannous fluoride, sodium monofluorophosphate, or zinc hexafluorosilicate which function to resist tooth decay. Other types of additives may include polymerization inhibitors, such as tert-butylo hydroytoluene (BHT), hydroquinone (HQ), and methylhydroquinone (MEHQ) which function to enhance the cement's resistance to adverse storage conditions.

The following examples illustrate some of the preferred forms of the invention, it being understood that the invention is not to be limited to the illustrated embodiments.

EXAMPLE 1

| Ingredients - 1st Component | Wt. % | Ingredients - 2nd Component | Wt. % |
|---|---|---|---|
| Bis-GMA | 50 | Bis-GMA | 34 |
| Triethylene glycol dimethacrylate | 38 | Triethylene glycol dimethacrylate | 20 |
| N, N Bis (2-hydroxyethylo)-p-toluidine | 1.8 | Powdered quartz | 40 |
| Silica | 3.2 | Benzoyl peroxide | 1.0 |
| Hydroxyethyl methacrylate | 7 | Hydroxyethyl methacrylate | 5 |

It will be understood that each component is separately packaged so that as hereinabove described, the first component is first coated onto the inner walls of a properly prepared post hole and the second component is then injected into the post hole, preferably by syringing, so no mixing of the two components is required. The post is then immediately inserted into the post hole before the cement sets. The cement is rendered self curing on contact and in a matter of minutes, the post is firmly secured so that it cannot be twisted or pulled out of the post hole.

EXAMPLE 2

The cement was formulated as follows:

| Ingredients - 1st Component | Wt. % | Ingredients - 2nd Component | Wt. % |
|---|---|---|---|
| Ethoxylated Bis-phenol A dimethacrylate | 20 | (Same as in Example 1) | |
| Tetrahydrofurfuryl methacrylate | 6.5 | | |
| Ethylene glycol dimethacrylate | 20 | | |
| Hydroxpropyl methacrylate | 19 | | |
| Polyethyl methacrylate | 30 | | |
| N, N dimethylo-p-toludine | 2.5 | | |
| Silica | 2.0 | | |

The application technique of the formulation of Example 2 is the same as hereinabove described except that before cementing the post hole, it was thoroughly dried using a mixture of alcohol and ethyl ether.

EXAMPLE 3

The cement was formulated as follows:

| Ingredients - 1st Component | Wt. % | Ingredients - 2nd Component | Wt. % |
|---|---|---|---|
| Polyalkyleneglycol dimethacrylate | 42 | Polyalkyleneglycol dimethacrylate | 12 |
| Diglycidyl ether of Bis-phenol A Dimethacrylate (Bis-GMA) | 8.0 | Diglycidyl ether of Bis-phenol A Dimethacrylate (Bis-GMA) | 16 |
| Ethyl/methyl methacrylate polymer | 28 | Powdered Glass | 68 |
| N, N Bis (2-hydroxyethylo)-p-toluidine | 2.0 | Silica | 3.3 |
| Hydroxyethyl methacrylate | 20 | Benzoyl peroxide | 0.7 |

The recommended application technique of the formulation of Example 3 is the same as described with respect to the formulation of Example 1.

It will be understood that the formation of the instant invention may include a releasable fluoride. A releasable fluoride may be included in the above formulae by the incorporating therein 0.1 to 0.5% by weight of sodium fluoride, which is preferably added to the paste or second component.

As noted herein, the cement may also be used to set a crown or bridge. After the tooth has been properly prepared to receive a crown or bridge, the crown or bridge is secured to the prepared tooth by applying one of the components to the prepared tooth and the other component to the under surface of the crown or bridge that receives the prepared tooth. As the crown or bridge is placed into firm contact with the component coating on the prepared tooth, the component coating on the under surface of the crown or bridge is brought into firm contact with the component coating on the prepared surface of the tooth, the respective components reacting on contact and pressure to immediately set to secure the crown or bridge in place onto the tooth. Any excess cement that extrudes beyond the periphery of the crown or bridge can be readily removed, since the excess material tends to set or harden at a much slower rate when not subject to firm contact. Thus, the excess cement material can be readily removed simply and quickly.

FIGS. 6 and 7 illustrate the procedure or method of securing a crown or bridge to a prepared tooth. As shown in FIG. 6, the tooth 10A has been prepared or shaped to receive the crown or bridge 20. The outer surface 10B of the tooth 10A is preferably coated with the primer or first component 12, as hereinbefore described. Also, the under surface 20A of the crown or bridge 20 is also preferably coated with the primer or first component of the cement formulation herein described.

The second component 15, as herein described, may be layed on top of either the primer layer 12 on the under surface of the crown or bridge or on top of the primer layer 12 on the surface 10B of the prepared tooth 10A. With the crown or bridge 20 coated, as described, the crown or bridge 20 is simply pressed firmly onto the coated portion 10B of the prepared tooth whereby the interaction of the respective components and applied pressure causes the formulation to set to firmly secure the crown or bridge 20 to the prepared tooth. Any excess of the described formulation which extrudes beyond the periphery of the crown or bridge 20 can be readily removed as the extruded material sets at a much slower rate than component layers 12 and 15 in firm contact between the coated under surface 20A of the crown or bridge 20 and the outer surface 10B of the prepared tooth 10A.

FIG. 7 is a view similar to FIG. 6, but illustrating a prepared tooth 10C having a core build up portion 10D prepared to receive a crown or bridge 20'. In all other respects, the procedure or method of securing the bridge or crown 20' to a tooth 10C having a core build up portion 10D is similar to that hereinabove described with respect to FIG. 6.

It will be understood that the crown or bridge of FIGS. 6 and 7 may be satisfactorily secured to the prepared tooth 10A or 10C simply by coating the undersurface of the bridge or crown with one of the described components and coating the outer surface of the prepared tooth with the other of the described component. In this simplified method, the crown or bridge 20 or 20' so coated may be firmly secured to the coated surface of the prepared tooth 10A or 10C respectively, simply by bringing the crown or bridge into contact with the coated tooth.

FIG. 7 illustrates the crown or bridge in the set position, while FIG. 6 illustrates the crown or bridge 20A about to be placed into firm contact with the prepared tooth for purposes of illustration.

The formulation of the cement described herein has exhibited superior adhesive or holding characteristics over previously known dental post cements. Initial testing conducted by the University of Texas have exhibited that in pull tests, it took 46 kg. of force to extract the dental post set in cement as described herein, as compared to a force of 22 kg. for a prior art, two component, self cured post cements. The test was conducted using a steel Para Post set in a post hole. In a similar test using glass fiber Fibrekor posts, the post itself broke before it could be pulled out of the post hole.

From the foregoing description, it will be apparent that the method of placing a dental post, crowns or bridges is effected by using a two part, self curing cement formulation which requires no pre-mixing prior to use, and which requires no pre-application of any bonding agent to a prepared tooth. The described method enables one to place and secure a dental post, crown or bridge to a prepared tooth simply and quickly in a minimum amount of time and with little effort.

While the disclosure is directed to preferred methods of placing a dental post in a prepared tooth and/or securing crowns and bridges thereto, and various cement formulations to accomplish the same, variations and modifications may be made without departing from the spirit or scope of the invention.

What is claimed is:

1. A method of placing a dental post in a tooth comprising the steps of:
   forming a post hole in the dentin portion of a tooth to be restored,
   coating the interior surface of said dentin portion of said post hole with a first component of a no-mix, two component, self curing cement,
   placing a second component of said no-mix, two component, self curing cement into said coated dentin portion of said post hole, and
   inserting a dental post into said post hole before said cement components set whereby said first and second components chemically set by contact to firmly secure said dental post within said dentin portion of said post hole.

2. A method as defined in claim 1 and including the step of conditioning said post hole with a dentin conditioner and thereafter washing and drying said post hole prior to said step of coating the interior surface of said post hole.

3. The method as defined in claim 1 and including the step of coating said first component onto the interior surface of said dentin portion of said post hole with a micro brush applicator.

4. The method as defined in claim 1 and including the step of placing said second component into said coated post hole by syringing said second component.

5. A no-mix, two component, self curing dental cement comprising:
   a first and second component,
   each of said components including a methacrylate resin,
   one of said components including an aromatic tertiary amine, and
   the other of said components including an organic peroxide
   wherein
   at least one of said components includes a hydrophilic monomer.

6. A no-mix, two component, self curing dental cement as defined in claim 5, wherein said organic peroxide comprises benzoyl peroxide.

7. A no-mix, two component, self curing dental cement as defined in claim 5, wherein said hydrophilic monomer is selected from the group consisting of hydroxyethyl methacrylate and hydroxypropyl methacrylate.

8. A no-mix, two component, self curing dental cement as defined in claim 5, wherein each a said components includes a filler.

9. A no-mix, two component, self curing dental cement as defined in claim 8, wherein said filler is selected from a group consisting of glasses, quartz, zirconium, oxide, silica, aluminum oxide, polyethylene, barium sulfate, calcium sulfate, titanium oxide, calcium phosphate, calcium silicate (Wollastonite), diatomaceous earth and bentonite.

10. A no-mix, two component, self curing dental cement as defined in claim 9, wherein said filler has a particle size ranging from 0.05 microns to 70 microns.

11. A no-mix, two component, self curing dental cement as defined in claim 5, wherein at least one of said components includes a fluoride salt selected from the group consisting of sodium fluoride, stannous fluoride, sodium monofluorophosphate, and zinc hexafluorosilicate.

12. A no-mix, two component, self curing dental cement as defined in claim 5 wherein at least one of said components includes a polymerization inhibitor.

13. A no-mix, two component, self curing dental cement as defined in claim 12, wherein said polymerization inhibitor is selected from the group consisting of tert-butylo hydroxytoluene (BHT), hydroquinone (HQ) and methylhydroquine (MEHQ).

14. A no-mix, two component, self curing dental cement as defined in claim 5, wherein said methacrylate resin is selected from the group consisting of Diglycidyl ether of bis-phenol A dimethacrylate (commonly known in the industry as Bis-GMA); alkylene glycol dimethacrylates, selected from the group consisting of ethylene, diethylene, triethylene and polyethylene glycol dimethacrylate, trimethylolopropane trimethacrylate; hydroxyethyl methacrylate; hydroxypropyl methacrylate; tetrahydzofurfuyl methacrylate; Bis-phenol A dimethacrylate, 7,7,9-trimethylo-4, 13 dioxo-3,4-dioxa-5 diazahexadecane-1,6 diol dimethacrylate (known in the industry as diurethane dimethacrylate) hexanediol dimethacrylate and cyclohexanediol dimethacrylate.

15. A no-mix, two component, self curing dental cement as defined in claim 14, wherein said methacrylate resins comprise 20% to 98% by weight of said dental cement.

16. A no-mix, two component, self curing dental cement as defined in claim 5 wherein said tertiary aromatic amine is selected from the group consisting of N,N Bis(2-hydroxyethylo)-p-toluidine; N,N Bis(2-hydroxypropylo),-p toluidine; N,N dimethylo-p-toluidine; N,N-diethylo-p-toluidine.

17. A no-mix, two component, self curing dental cement as defined in claim 5 and including a thickening agent.

18. A no-mix, two component, self curing dental cement as defined in claim 17, wherein said thickening agent is selected from the group consisting of a polyacrylic acid having a molecular weight of about 200,000, and a polyalkylene such as polybutenes and poly-C1–C3 alkyl methacrylates.

19. A no-mix, two component, self curing dental cement comprising:
   a first and second component,
   each of said components including a methacrylate resin,
   one of said components including an aromatic tertiary amine, and
   the other of said components including an organic peroxide
   wherein both of said components include a hydrophilic monomer.

20. A method of setting a dental post in the dentin portion of a post hole formed in a prepared tooth comprising the steps of:
   using a two component, no-mix, self curing cement wherein each of said components includes a polyrnerizable methacrylate resin matrix,
   one of said components containing a tertiary aromatic amine, and
   the other of said components including organic peroxide,
   coating the surface of a dental post with one of said components, and placing the other of said components in the dentin portion of a post hole, and
   inserting the coated dental post into the post hole containing the other of said component whereby the respective components by contact set to firmly secure the dental post within the post hole.

21. The method as defined in claim 20, wherein said resin mix includes up to 70% of Bis-GMA.

22. The method as defined in claim 20, wherein said resin mix includes up to 40% of a hydroxyalkylmethacrylate selected from the group consisting of hydroxyethyl methacrylate and hydroxypropyl-methacrylate.

23. A method of placing a dental prosthesis onto a dentin portion of a tooth comprising the steps of:
   preparing a tooth to expose the dentin portion to be restored,
   preparing a prosthesis to be secured to the dentin portion of said prepared tooth,
   coating the surface of the prosthesis to be placed onto said dentin portion of said prepared tooth with one component of a two component, no mix, self curing cement,
   coating the surface of the exposed dentin portion of said prepared tooth for receiving the prosthesis with the other component of a two component, no mix self curing cement, and
   placing said coated portion of said prosthesis into firm contact with the coating portion of said prepared tooth whereby interaction of said first and second components by contact causes said components to set to firmly secure said prosthesis to said dentin portion of said prepared tooth.

24. The method as defined in claim 23 wherein each of said components includes a methacrylate resin, and
   one of said components including an aromatic tertiary amine, and
   the other of said components including an organic peroxide.

25. A method of placing a dental prosthesis onto a tooth comprising the steps of:
   preparing a tooth to be restored,
   preparing a prosthesis to be secured to the prepared tooth,
   coating the surface of the prosthesis receiving the prepared tooth with one component of a two component, no mix, self curing cement,
   coating the surface of the prepared tooth for receiving the prosthesis with the other component of a two component, no mix, self curing cement, and
   placing said coated portion of said prosthesis into firm contact with the coating portion of said prepared tooth whereby interaction of said first and second components on contact causes said components to set and firmly secures said prosthesis to said prepared tooth wherein at least one of said components includes a hydrophilic monomer.

26. The method as defined in claim 25 wherein one of said components comprises a moderately viscous liquid and the other of said components comprises a lightly filled paste.

27. The method as defined in claim 26 wherein each of said components comprises a methacrylate resin in a range of 20% to 98% by weight,
and one of said components including 1% to 12% by weight of an aromatic tertiary amine, and
the other of said component including 0.3% to 5% by weight of an organic peroxide.

28. The method as defined in claim 27 wherein at least one of said components includes at least 1% to 25% by weight of a hydrophilic monomer.

29. The method as defined in claim 27 wherein one of said components includes 0.1 to 0.5% by weight of a releasable fluoride.

30. The method as defined in claim 29 wherein said releasable fluoride comprises sodium fluoride, and
said sodium fluoride is incorporated into said lightly filled paste component.

31. A method of securing a dental prosthesis onto a dentin portion of a prepared tooth comprising the steps of:
coating the contacting surfaces of the dental prosthesis and the dentin portion of a prepared tooth with a coating of a first component of a two component no mix curing cement,
placing a layer of the other component onto one of said coated contacting surfaces, and
placing the coated contacting surface of the prosthesis into firm contact with the coated dentin portion, contacting surface of the prepared tooth.

* * * * *